United States Patent
Daiku et al.

(10) Patent No.: US 10,720,256 B2
(45) Date of Patent: Jul. 21, 2020

(54) ELECTRON BEAM IRRADIATING DEVICE

(71) Applicant: HITACHI ZOSEN CORPORATION, Osaka-shi, Osaka (JP)

(72) Inventors: Hiroyuki Daiku, Osaka (JP); Ichiro Sakai, Osaka (JP); Norihiro Inoue, Osaka (JP); Yohei Terasaka, Osaka (JP)

(73) Assignee: HITACHI ZOSEN CORPORATION, Osaka (JP)

( * ) Notice: Subject to any disclaimer, the term of this patent is extended or adjusted under 35 U.S.C. 154(b) by 0 days.

(21) Appl. No.: 16/348,340

(22) PCT Filed: Nov. 2, 2017

(86) PCT No.: PCT/JP2017/039788
§ 371 (c)(1),
(2) Date: May 8, 2019

(87) PCT Pub. No.: WO2018/088334
PCT Pub. Date: May 17, 2018

(65) Prior Publication Data
US 2019/0287693 A1    Sep. 19, 2019

(30) Foreign Application Priority Data
Nov. 9, 2016   (JP) .................................. 2016-218482

(51) Int. Cl.
*G21K 5/04*       (2006.01)
*A61L 2/08*       (2006.01)
(Continued)

(52) U.S. Cl.
CPC .................. *G21K 5/04* (2013.01); *A61L 2/08* (2013.01); *A61L 2/087* (2013.01); *B65B 55/04* (2013.01);
(Continued)

(58) Field of Classification Search
USPC ...................................................... 250/492.3
See application file for complete search history.

(56) References Cited

U.S. PATENT DOCUMENTS

| 4,112,307 A * | 9/1978 | Foll .......................... H01J 33/04 250/492.3 |
| 4,434,372 A | 2/1984 | Cleland |

(Continued)

FOREIGN PATENT DOCUMENTS

| GB | 1225905 | 3/1971 |
| JP | 55-120000 | 2/1954 |

(Continued)

OTHER PUBLICATIONS

International Search Report dated Jan. 23, 2018 issued in corresponding International Patent Application No. PCT/JP2017/039788 with English translation.

(Continued)

*Primary Examiner* — Kiet T Nguyen
(74) *Attorney, Agent, or Firm* — Pillsbury Winthrop Shaw Pittman, LLP

(57) ABSTRACT

Provided is an electron beam irradiating device capable of emitting an electron beam from an electron beam generation source surrounded by a vacuum chamber to outside of the vacuum chamber through an electron beam exit window. The electron beam exit window includes: a grid; a window foil allowing the electron beam to pass therethrough; and a frame-shaped pressing member pressing the window foil against the grid. The surface of the grid has a groove section having an annular shape. A metal gasket is pressed between the groove section and the window foil.

3 Claims, 3 Drawing Sheets

(51) Int. Cl.
  *B65B 55/08* (2006.01)
  *B67C 7/00* (2006.01)
  *G21K 5/00* (2006.01)
  *H01J 5/18* (2006.01)
  *H01J 5/22* (2006.01)
  *B65B 55/04* (2006.01)

(52) U.S. Cl.
  CPC ............ *B65B 55/08* (2013.01); *B67C 7/0073* (2013.01); *G21K 5/00* (2013.01); *H01J 5/18* (2013.01); *H01J 5/22* (2013.01)

(56) References Cited

U.S. PATENT DOCUMENTS

| | | | |
|---|---|---|---|
| 5,483,074 A | 1/1996 | True | |
| 5,621,270 A * | 4/1997 | Allen | B01D 53/323 |
| | | | 250/492.3 |

FOREIGN PATENT DOCUMENTS

| | | |
|---|---|---|
| JP | 5012198 U | 2/1975 |
| JP | 61-038500 A | 2/1986 |
| JP | 9-203800 A | 8/1997 |
| JP | 2001-013300 A | 1/2001 |
| JP | 2004-258011 A | 9/2004 |
| JP | 2005-172449 A | 6/2005 |
| JP | 2005-255497 A | 9/2005 |
| JP | 2010-008386 A | 1/2010 |
| JP | 2013-160721 A | 8/2013 |

OTHER PUBLICATIONS

Extended European Search Report EP Application No. 17869899.9 dated Oct. 7, 2019.
Notice of Reasons for Refusal dated Jan. 21, 2020 issued in corresponding Japanese Patent Application No. 2016-218482 with English translation.
Notice of Reasons for Refusal dated Mar. 31, 2020 issued in corresponding Japanese Patent Application No. 2016-218482 with English translation.

* cited by examiner

ELECTRON BEAM IRRADIATING DEVICE

CROSS-REFERENCE TO RELATED APPLICATIONS

This application is the U.S. National Phase of PCT/JP2017/039788, filed Nov. 2, 2017, which claims the benefit of priority from Japanese Patent Application Serial No. 2016-218482, filed Nov. 9, 2016, the contents of each of which are hereby incorporated by reference in entirety.

TECHNICAL FIELD

The present invention relates to an electron beam irradiating device which is used for performing sterilization processing for beverage bottles or medical containers, for example.

BACKGROUND ART

As shown in FIGS. 1 and 2, an electron beam irradiating device 1 includes an electron beam generation source 2, a vacuum chamber 3 which surrounds the electron beam generation source 2, and an electron beam exit window 4 attached to the vacuum chamber 3. The wall surface of the vacuum chamber 3 is partially cut away, and the electron beam exit window 4 is provided to this portion from which the wall surface is cut away. That is, a closed space is formed by the vacuum chamber 3 and the electron beam exit window 4. A vacuum pump P is connected to the vacuum chamber 3. The closed space can be brought into a vacuum state by the vacuum pump P. The electron beam exit window 4 includes a window foil which allows an electron beam B to pass therethrough. An electron beam generated from the electron beam generation source 2 exits the vacuum chamber 3 through this window foil. Reference numeral 5 in FIG. 1 and FIG. 2 denotes an extraction electrode for extracting electrons excited in the electron beam generation source 2.

The inside of the vacuum chamber 3 is evacuated by the vacuum pump P. At this point of operation, the window foil functions as a partition wall between a vacuum atmosphere and the atmosphere and hence, an atmospheric pressure is applied to the window foil. In addition, the window foil is formed with a small thickness of approximately several μm to 10 μm in order to increase transmissivity of the electron beam B. Further, the window foil absorbs a part of the electron beam B, thus generating heat. Accordingly, the window foil significantly deteriorates compared with other components of the apparatus, thus easily causing a trouble. For this reason, the window foil may be periodically replaced even if there is no malfunction or a problem caused by deterioration.

For example, patent literature 1 discloses the configuration where a window foil is attached to an electron beam irradiating device. Patent literature 1 discloses the following configuration. A grid is attached to a vacuum chamber, the surface of the grid has an annular groove, a window foil is made to overlap with the annular groove in a state where an O-ring is disposed in the annular groove, a pressing member is further made to overlap with the window foil, and the grid and the pressing member are fastened to each other with bolts, thus attaching the window foil to the electron beam irradiating device. With such a configuration, gas sealing property in the vacuum chamber can be ensured, and the window foil can be easily replaced by loosening the bolts and by removing the pressing member.

CITATION LIST

Patent Literature

Patent Literature 1: Japanese Patent No. 2013-160721

SUMMARY OF INVENTION

Technical Problem

In bringing the inside of the vacuum chamber into a vacuum state, heating (hereinafter also referred to as "baking") may be applied to the inside of the vacuum chamber so as to remove impurities in the inside of the vacuum chamber, thus improving vacuum capability. A material for forming an O-ring is not clearly described in patent literature 1. However, it is general to consider that rubber (organic resin) is used as the material for forming the O-ring. The O-ring made of rubber has a low softening temperature, thus having low heat resistance. Accordingly, when the O-ring is exposed to a high temperature environment due to baking or the like, the O-ring is softened, thus causing the window foil and the grid to be joined to each other. Therefore, there is a possibility that the replacement of the window foil becomes difficult. Accordingly, it is an object of the present invention to allow the window foil to be easily replaced even in the case where the electron beam exit window is exposed to a high temperature environment.

Solution to Problem

According to the present invention, there is provided an electron beam irradiating device which is capable of emitting an electron beam from an electron beam generation source surrounded by a vacuum chamber to outside of the vacuum chamber through an electron beam exit window, the electron beam exit window including: a grid; a window foil allowing the electron beam to pass through the window foil; and a frame-shaped pressing member pressing the window foil against the grid, wherein a surface of the grid has a groove section having an annular shape, and a metal gasket is pressed between the groove section and the window foil.

Advantageous Effects of Invention

According to the present invention, the window foil is pressed between the grid and the pressing member. Further, the metal gasket is pressed between the annular groove section, provided to the surface of the grid, and the window foil. With such a configuration, gas sealing property in the vacuum chamber can be ensured, and the window foil can be easily replaced by removing the pressing member. Further, the metal gasket generally has a higher softening temperature than an O-ring made of rubber, thus having higher heat resistance than the O-ring made of rubber. Accordingly, even under a high temperature environment due to baking or the like, it is possible to avoid a situation where the gasket causes the window foil and the grid to be joined to each other. Eventually, the window foil can be easily replaced.

DESCRIPTION OF EMBODIMENTS

Figure 1:
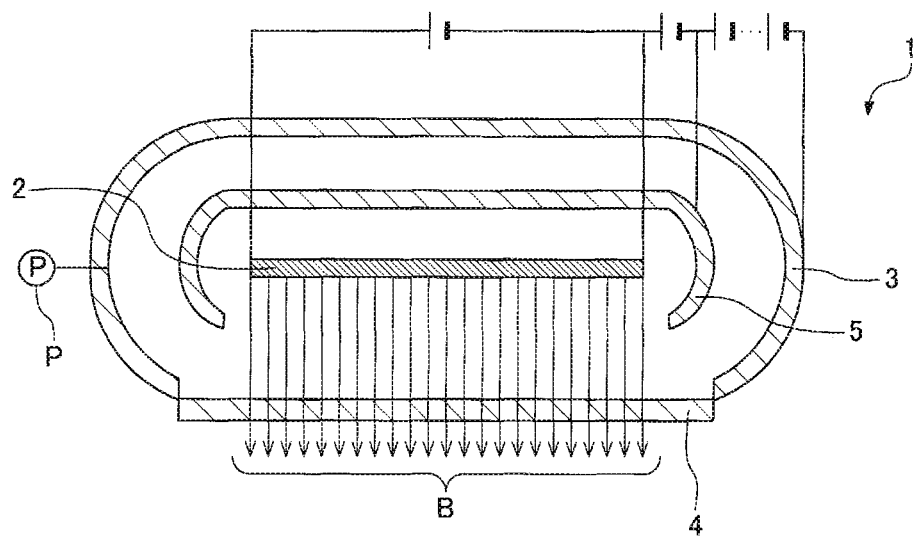
FIG. 1 is a cross-sectional view of a general electron beam irradiating device as viewed in a front view.
Figure 2:
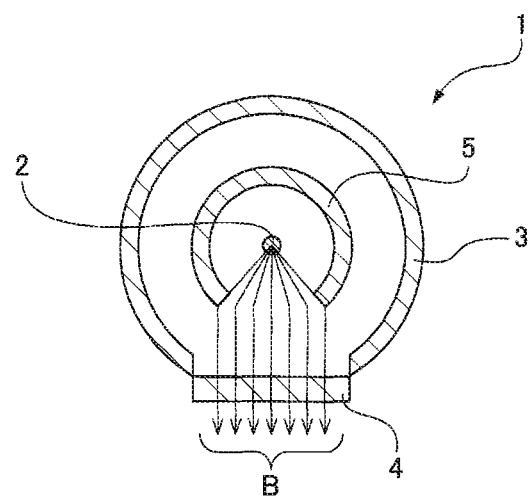
FIG. 2 is a cross-sectional view of the general electron beam irradiating device as viewed in a side view.

An electron beam irradiating device according to this embodiment is described in detail with reference to drawings. Components of the electron beam irradiating device according to this embodiment other than an electron beam exit window 4 are substantially identical to those of the general electron beam irradiating device shown in FIGS. 1 and 2. Accordingly, the detailed description of the configuration of the electron beam irradiating device is omitted. Any components may be used as the components of the electron beam irradiating device other than the electron beam exit window 4 provided that the electron beam irradiating device 1 can emit an electron beam B to outside of a vacuum chamber 3.

Hereinafter, the configuration of the electron beam exit window 4 is described in detail.

Figure 3:
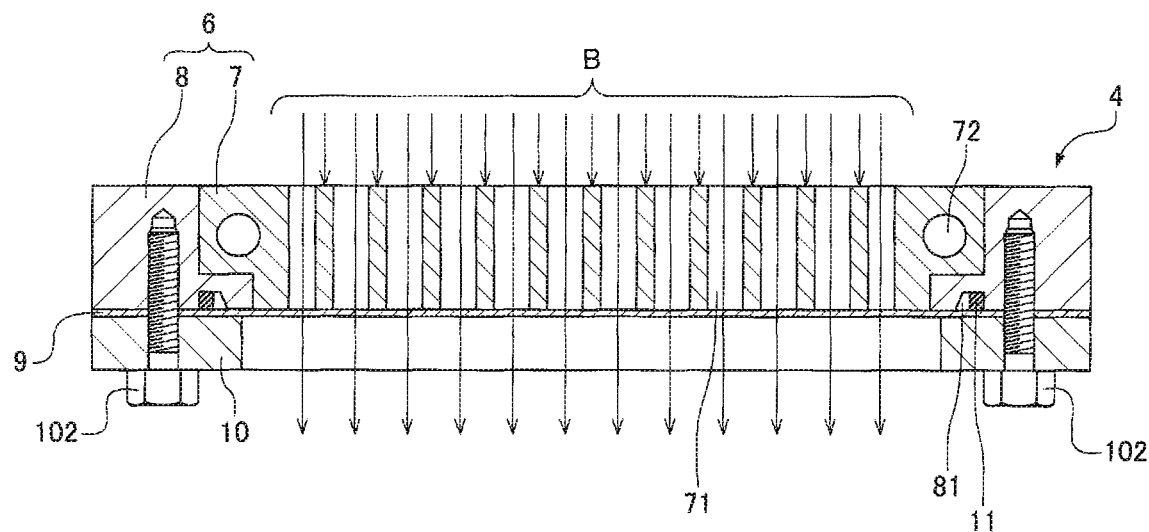
FIG. 3 is a cross-sectional view of an electron beam exit window of an electron beam irradiating device according to this embodiment.
Figure 4:
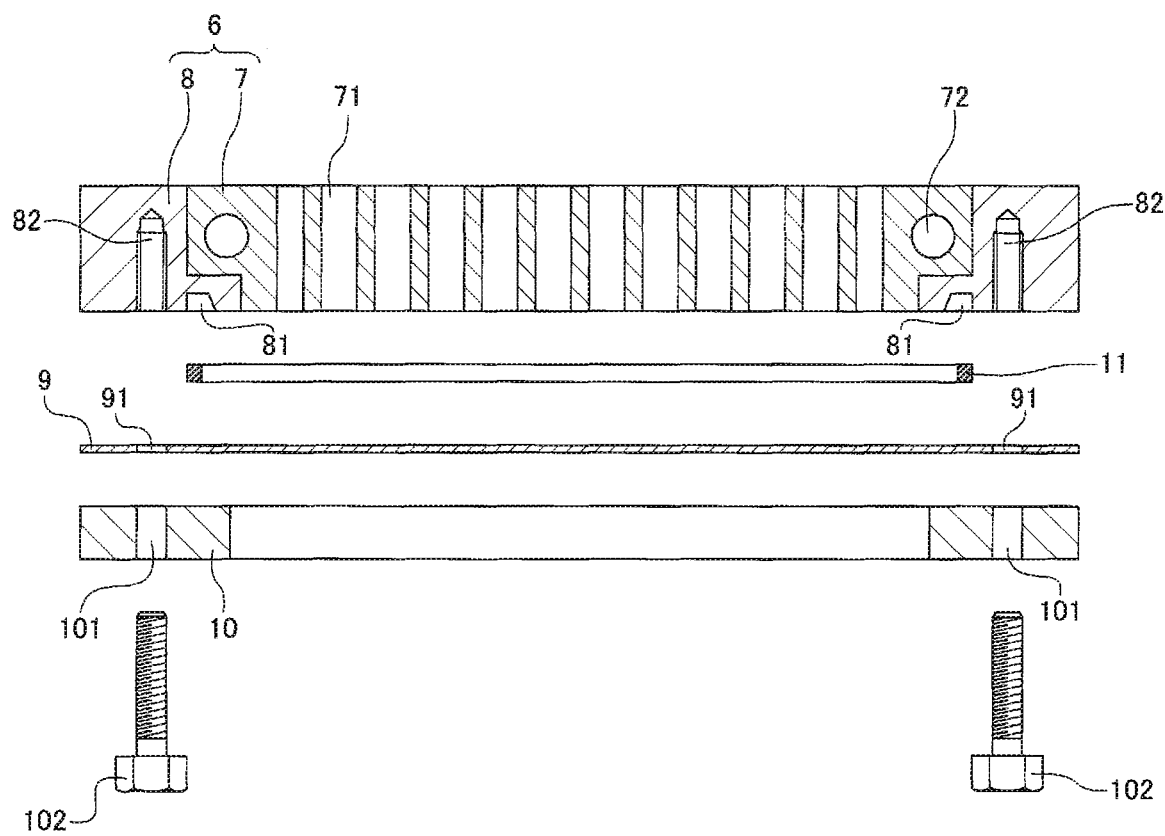
FIG. 4 is a cross-sectional view of the electron beam exit window of the electron beam irradiating device in a disassembled state.

FIG. 3 is a cross-sectional view of the electron beam exit window 4 according to this embodiment. FIG. 4 is a cross-sectional view of the electron beam exit window 4 in a disassembled state. As shown in FIGS. 3 and 4, the electron beam exit window 4 includes a grid 6, a window foil 9, a frame-shaped pressing member 10, and a metal gasket 11. The grid 6 is formed of a grating region 7 allowing an electron beam to pass therethrough, and an outer peripheral region 8 formed around the grating region 7.

Figure 5:
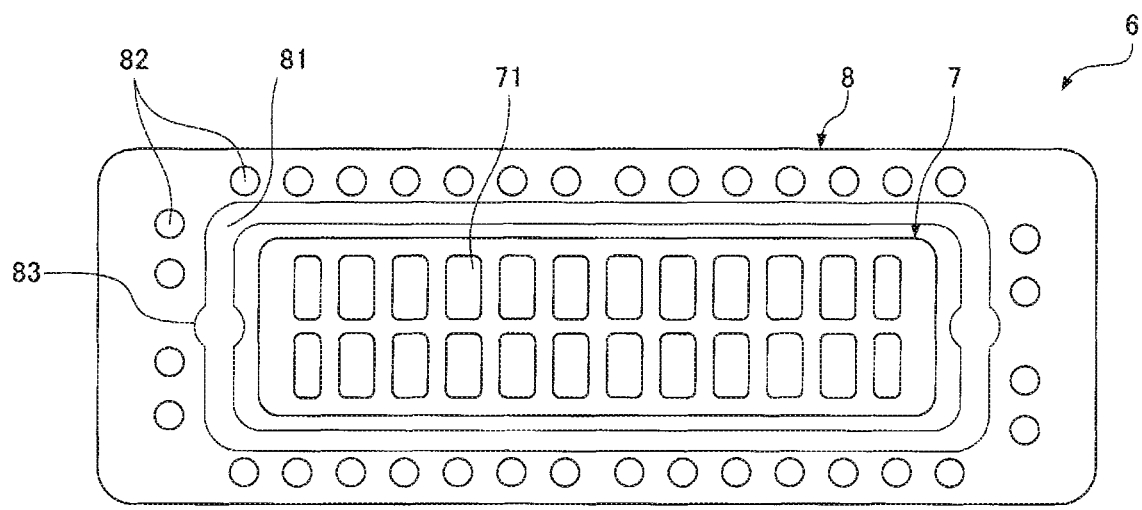
FIG. 5 is a bottom view of a grid of the electron beam exit window.

As shown in FIGS. 3 to 5, the grating region 7 of the grid 6 is formed by arranging a plurality of hole portions 71. The electron beam B passes through the hole portions 71. The hole portion 71 may have any shape in transverse cross section provided that the hole portion allows an electron beam to pass therethrough. For example, the hole portion 71 may have a circular shape or a polygonal shape in transverse cross section. Electrons impinge on portions of the grating region 7 other than the hole portions 71 so that such portions of the grating region 7 reach a high temperature. For this reason, a cooling circuit 72 is provided to the outer peripheral end of the grating region 7. A refrigerant, such as water, passes through the cooling circuit 72. Further, in order to increase cooling efficiency of the cooling circuit 72, it is preferable that the grating region 7 be made of a material having high thermal conductivity. For example, the grating region 7 is made of copper.

The outer peripheral region 8 of the grid 6 is a region formed around the grating region 7. A vacuum chamber is connected to the outer peripheral region 8. The surface of the outer peripheral region 8 has a groove section 81 having an annular shape. The metal gasket 11 is disposed in the groove section 81. Further, the outer peripheral region 8 is made of a material different from a material for forming the grating region 7. The outer peripheral region 8 is made of a material having a higher softening temperature than the grating region 7. For example, the outer peripheral region 8 is made of stainless steel. The outer peripheral region 8 also has screw holes 82 for bolts. Reference numeral 83 in FIG. 5 denotes a tab groove formed in the groove section 81 for picking up the gasket 11 with tweezers or the like at the time of replacing the gasket 11.

The window foil 9 is provided between the grid 6 and the pressing member 10. The window foil 9 has through holes 91 each of which allows a bolt to pass therethrough. As a material for forming the window foil 9, a material with a thickness is used which allows an electron beam to pass through the material. For example, a titanium foil with a thickness of approximately several μm to 10 μm is used. The window foil 9 functions as a partition wall between a vacuum atmosphere and the atmosphere.

Figure 6:
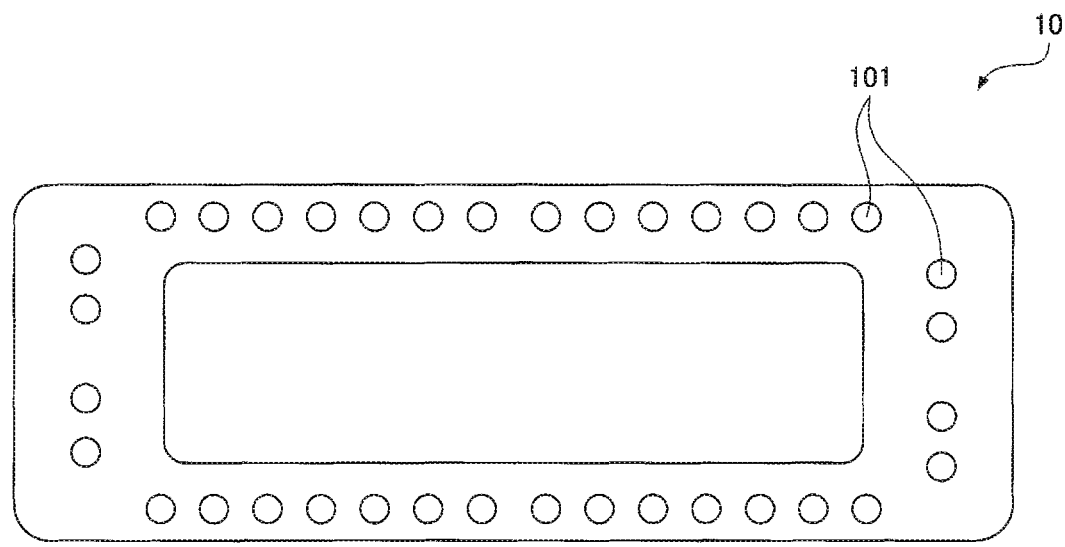
FIG. 6 is a bottom view of a pressing member of the electron beam exit window.

As shown in FIGS. 3, 4 and 6, the frame-shaped pressing member 10 is disposed to substantially overlap with the outer peripheral region 8 without overlapping with the grating region 7 of the grid 6. The pressing member 10 has through holes 101 for bolts. Each bolt 102 passes through the screw hole 101, formed in the pressing member 10, and the through hole 91, formed in the window foil 9, and the bolt 102 is fastened to the screw hole 82 formed in the outer peripheral region 8 of the grid 6. With such fastening, the window foil 9 is pressed between the pressing member 10 and the grid 6. At this point of operation, the metal gasket 11 is pressed between the window foil 9 and the groove section 81.

As the metal gasket 11, a gasket is used which has an annular shape in the same manner as the groove section 81, and which has a height greater than the depth of the groove section 81. Fastening the bolts 102 causes the gasket 11 to be collapsed and deformed between the groove section 81 and the window foil 9. Due to such collapse and deformation, gas sealing property in the inside of the vacuum chamber can be ensured. As a material for forming the metal gasket 11, for example, stainless steel, gold, silver, lead, annealed copper or the like may be used. Any material may be used as a material for forming the metal gasket 11 provided that the material has lower hardness than a material for forming the window foil 9 and the groove section 81 at a normal temperature.

A conventional electron beam irradiating device uses an O-ring made of an organic resin in place of the metal gasket 11. The softening temperature of the O-ring made of an organic resin varies depending on the kind of organic resin. However, in the case where the O-ring is made of a general rubber, the softening temperature of the O-ring is approximately 100° C. Accordingly, when the O-ring is exposed to a high temperature environment where a temperature significantly exceeds 100° C. due to baking or the like, the O-ring causes the window foil 9 and the grid 6 to be joined to each other. Therefore, there may be a case where the replacement of the window foil 9 becomes difficult.

On the other hand, the electron beam irradiating device of this embodiment uses the metal gasket 11 in place of an O-ring made of an organic resin. Accordingly, even in the case where the metal gasket 11 is exposed to a high temperature environment due to baking or the like, it is possible to avoid a situation where the gasket 11 causes the window foil 9 and the grid 6 to be joined to each other. Eventually, the window foil 9 can be easily replaced. The softening temperature of the metal gasket varies depending on the kind, heat history and the like of metal used for the metal gasket 11. In the case where stainless steel is used to form the metal gasket 11, the softening temperature of the metal gasket 11 is approximately 600° C. to 700° C.

According to this embodiment, the grid 6 is formed of the grating region 7 allowing an electron beam to pass therethrough, and the outer peripheral region 8 formed around the grating region 7. The groove section 81 is provided to the surface of the outer peripheral region 8, and the outer peripheral region 8 is made of a material having a higher softening temperature than a material used for the grating region 7. With such a configuration, it is possible to avoid a situation where the replacement of the gasket 11 becomes difficult. Hereinafter, the description is made in detail.

As previously described, an electron beam impinges on the grating region 7 of the grid 6 so that the grating region 7 reaches a high temperature. Accordingly, it is preferable that the grating region 7 be made of a material having high thermal conductivity for cooling. For example, the grating region 7 is made of copper. Although the softening temperature of copper varies depending on heat history and the like of copper, the softening temperature of copper is approximately 200° C. to 400° C. Assume the case where all region of the grid 6 is made of copper. In such a case, if the outer peripheral region 8 of the grid 6 is exposed to a high temperature environment of 200° C. or more due to baking or the like, the outer peripheral region 8 is softened and joined to the gasket 11. Accordingly, there is a possibility that the replacement of the gasket 11 becomes difficult. If the gasket 11 is joined to the grid 6, thus forming an integral body, the gasket 11 loses a function as a gasket so that gas sealing property in the vacuum chamber is lowered.

On the other hand, according to this embodiment, even in the case where copper is used as a material for forming the grating region 7 in order to ensure thermal conductivity of the grating region 7 of the grid 6, a material having a higher softening temperature than the grating region 7 is used as a material for forming the outer peripheral region 8, on which the groove section 81 is formed. Accordingly, compared with the case where all region of the grid 6 is made of copper, it is possible to avoid a situation where the replacement of the gasket 11 becomes difficult. In other words, in the case where the softening temperature of the outer peripheral region 8 of the grid 6 is higher than the softening temperature of the grating region 7 by 100° C., for example, the upper limit value of a baking temperature increases by 100° C. compared with the case where both the outer peripheral region 8 and the grating region 7 have the same softening temperature. Increasing a baking temperature reduces the amount of impurities in the vacuum chamber, thus improving vacuum capability.

The material used for the outer peripheral region 8 may be stainless steel, for example. As previously described, the softening temperature of stainless steel is approximately 600° C. to 700° C. A material having higher softening temperature than copper may be chromium, silver, titanium, nickel and the like, in addition to stainless steel. Stainless steel has lower thermal conductivity than copper. Accordingly, using copper is more preferable than using stainless steel to form the grating region 7.

The grating region 7 and the outer peripheral region 8 are joined to each other using a method, such as a Hot Isostatic Pressing (HIP), welding or the like. In the case where the grating region 7 and the outer peripheral region 8 are joined to each other using a Hot Isostatic Pressing, the grid 6 forms a functionally graded material of a material of the grating region 7 and a material of the outer peripheral region 8. When the grid 6 is made of a functionally graded material, leakage of a gas from between the grating region 7 and the outer peripheral region 8 can be prevented with certainty compared with the case where the grid 6 is formed by welding or the like. Accordingly, gas sealing property in the vacuum chamber can be improved.

It is preferable that the groove section 81 include corner portions forming the groove section 81, and the corner portions which come into contact with the window foil 9 on the inner peripheral side of the groove section have an obtuse angle. This is because such a configuration can prevent the window foil 9 from being torn at the corner portion of the groove section 81 on the inner peripheral side. The corner portion forming the groove section 81 is not limited to a corner in a strict meaning, and also includes a rounded corner.

It is preferable that the gasket 11 has a rectangular shape in cross section as shown in FIGS. 3 and 4. In the case where the gasket 11 has a rectangular shape in cross section, for example, a contact surface area between the gasket 11 and the bottom surface of the groove section 81, and a contact surface area between the gasket 11 and the window foil 9 increase compared with the case where the gasket 11 has a circular shape in cross section. Accordingly, it is possible to improve gas sealing property in the vacuum chamber. The shape of the gasket 11 in cross section is not limited to a rectangular shape, and may be a trapezoidal shape.

It is preferable that the cooling circuit 72 be disposed at a position close to the groove section 81. This is because such a configuration can prevent a situation where the gasket 11 thermal expands, thus lowering gas sealing property. For example, when the gasket 11 and the outer peripheral region 8 significantly differ from each other in coefficient of thermal expansion, the gasket 11 is displaced with respect to the groove section 81 due to thermal expansion so that gas sealing property in the vacuum chamber is lowered. On the other hand, when the gasket 11 is disposed at a position in the vicinity of the cooling circuit 72, it is possible to suppress the thermal expansion amount of the gasket 11 and the outer peripheral region 8 disposed around the gasket 11. Accordingly, even when the gasket 11 and the outer peripheral region 8 significantly differ from each other in coefficient of thermal expansion, it is possible to prevent lowering of gas sealing property caused by positional displacement of the gasket 11.

The following configuration may be considered in order to dispose the cooling circuit 72, provided to the grating region 7, at a position close to the groove section 81 formed on the outer peripheral region 8. For example, as shown in FIG. 3 and FIG. 4, an interface between the grating region 7 and the outer peripheral region 8 includes a stepped portion, and the cooling circuit 72 and the groove section 81 at least partially overlap with each other as viewed in a plan view (as viewed from a direction perpendicular to the window foil 9 or the like).

The electron beam irradiating device according to this embodiment adopts a mode where the grid 6 is formed of the grating region 7 and the outer peripheral region 8 which are made of different materials. However, the present invention is not limited to this mode. Assume the case where the grid 6 is made of a material of one kind. Also in such a case, even if the gasket 11 is exposed to a higher temperature environment, the window foil 9 can be replaced more easily compared with the case where an O-ring made of an organic resin is used as long as the metal gasket 11 is used.

The invention claimed is:

1. An electron beam irradiating device which is capable of emitting an electron beam from an electron beam generation source surrounded by a vacuum chamber to outside of the vacuum chamber through an electron beam exit window,
the electron beam exit window comprising:
a grid;

a window foil allowing the electron beam to pass through the window foil;

a frame-shaped pressing member pressing the window foil against the grid;

a grating region of the grid allowing the electron beam to pass through the grating region; and an outer peripheral region of the grid formed around the grating region using a material different from a material used for the grating region, wherein a surface of the grid has a groove section having an annular shape, a metal gasket is pressed between the groove section and the window foil, a softening temperature of the outer peripheral region is higher than a softening temperature of the grating region, and thermal conductivity of the grating region is higher than thermal conductivity of the outer peripheral region.

2. The electron beam irradiating device according to claim 1, wherein the groove section is formed on a surface of the outer peripheral region, a cooling circuit allowing a refrigerant to pass through the cooling circuit is provided to the grating region, and an interface surface between the grating region and the outer peripheral region is formed in a position between the cooling circuit and the groove section wherein the grating region and the outer peripheral region are connected at the interface surface.

3. The electron beam irradiating device according to claim 1, wherein the groove section having an annular shape includes corner portions forming the groove section, and a corner portion, which comes into contact with the window foil on an inner peripheral side of the groove section, has an obtuse angle.

* * * * *